(12) United States Patent
Chou

(10) Patent No.: US 7,442,930 B2
(45) Date of Patent: Oct. 28, 2008

(54) METHOD FOR CORRECTING DISTORTIONS IN ELECTRON BACKSCATTER DIFFRACTION PATTERNS

(75) Inventor: Cheng Tsien Chou, Oxford (GB)

(73) Assignee: Oxford Instruments Analytical Limited, Oxford (GB)

( * ) Notice: Subject to any disclaimer, the term of this patent is extended or adjusted under 35 U.S.C. 154(b) by 281 days.

(21) Appl. No.: 11/398,116

(22) Filed: Apr. 5, 2006

(65) Prior Publication Data
US 2006/0219903 A1    Oct. 5, 2006

(30) Foreign Application Priority Data
Apr. 5, 2005    (GB)    .................................. 0506907.5

(51) Int. Cl.
    *G01N 23/00*    (2006.01)
(52) U.S. Cl. ........................ 250/310; 250/311; 250/307; 250/492.3; 250/492.22; 250/550; 382/141; 382/151; 382/216; 382/296
(58) Field of Classification Search ................. 250/311, 250/310, 306, 307, 492.3, 492.22, 550; 382/141, 382/151, 216, 296; 359/521
See application file for complete search history.

(56) References Cited

U.S. PATENT DOCUMENTS

| | | | | |
|---|---|---|---|---|
| 6,326,619 | B1 * | 12/2001 | Michael et al. | ............. 250/310 |
| 6,555,817 | B1 * | 4/2003 | Rohde et al. | ................ 250/311 |
| 6,590,209 | B1 * | 7/2003 | Bajt | ........................... 250/307 |
| 6,664,544 | B1 * | 12/2003 | Marui et al. | .......... 250/396 ML |
| 2003/0057377 | A1 * | 3/2003 | Gilmore et al. | ............. 250/397 |
| 2004/0011958 | A1 * | 1/2004 | Wright et al. | ............... 250/307 |
| 2004/0188610 | A1 * | 9/2004 | Hirose | ........................ 250/310 |
| 2005/0103995 | A1 * | 5/2005 | Yanagiuchi et al. | ......... 250/309 |

* cited by examiner

*Primary Examiner*—Jack I. Berman
*Assistant Examiner*—Michael J Logie
(74) *Attorney, Agent, or Firm*—Vern Maine & Associates

(57) ABSTRACT

A method is provided for correcting magnetic field distortions in an electron backscatter diffraction (EBSD) pattern. An EBSD pattern is firstly generated from a sample placed within an electron microscope. A predetermined representation of a magnetic field in the microscope is used to calculate the trajectories of electrons in the microscope, for different emergence angles. A corrected EBSD pattern is then calculated using the calculated trajectories, the corrected EBSD pattern representing the EBSD pattern if the microscope magnetic field were substantially absent.

22 Claims, 11 Drawing Sheets

10 mm

Axial Magnetic Flux

Axial Magnetic Flux

FIGURE 9A
FIGURE 9B
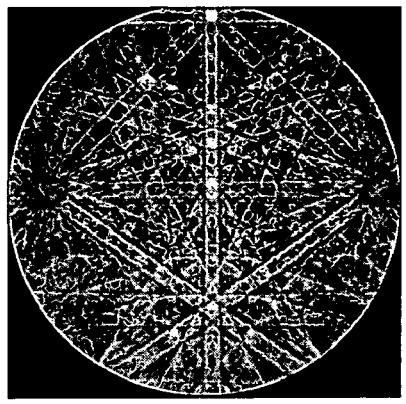
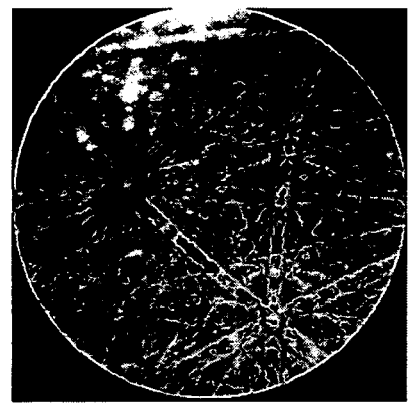
FIGURE 10A    FIGURE 10B    FIGURE 10C
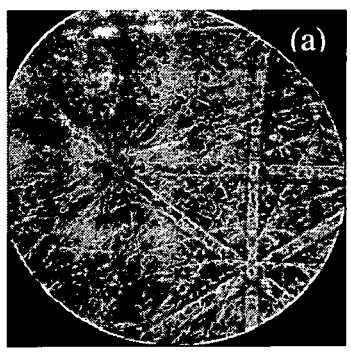
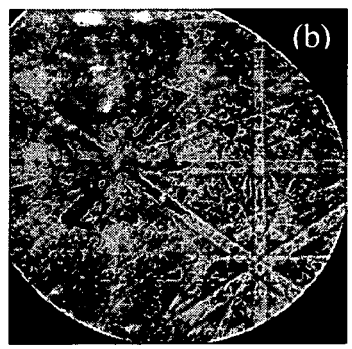
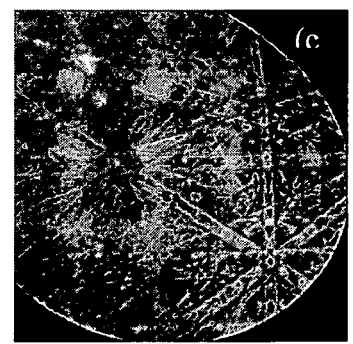

METHOD FOR CORRECTING DISTORTIONS IN ELECTRON BACKSCATTER DIFFRACTION PATTERNS

RELATED APPLICATIONS

This application claims the priority to GB Patent Application No. 0506907.5, filed Apr. 5, 2005.

FIELD OF THE INVENTION

The present invention relates to a method for correcting distortions in backscatter diffraction patterns obtained from crystalline specimens using an electron microscope.

BACKGROUND OF THE INVENTION

Scanning electron microscopes (SEMs) are used to magnify small samples by scanning a focused electron beam across the surface. An SEM may also be used to obtain crystallographic information such as the size and shape of crystals or grains, the orientation of crystal lattices, and the spatial location of the crystals within a polycrystalline material.

When the electron beam in the SEM strikes the desired point upon the sample, the electrons interact with a small volume of the material and scattered electrons are diffracted by the crystal lattice so that an electron backscatter diffraction (EBSD) pattern is generated on a phosphor screen within the SEM. The screen is monitored using a low light level integrating CCD device. The CCD signal provides a digital image of the diffraction pattern for analysis by the computer which is a 2-D array of picture elements with individual intensity values. The diffraction patterns formed on the screen take the form of "Kikuchi bands" which are pairs of near straight lines. The bands show the traces of the diffracted electron beam on the phosphor plate that satisfy the Bragg conditions in the crystal. The relative spacing and angles of the bands contain information describing the orientation of the crystal under the electron beam, with respect to the beam and the phosphor screen.

The orientation of the crystal is determined by software running on the SEM computer using the Kikuchi bands in the diffraction pattern and the crystallographic information contained in a crystal structure database. This is performed using an image processing routine known as a "Hough transform" in which each pair of bands in the pattern is transformed into a spot in "Hough space". The angular coordinates of the spot in Hough space provide the inclination angle of the Kikuchi band and the distance of the band to a selected origin. In analyzing the diffraction pattern, the software commonly selects three strong and non-coplanar Kikuchi bands in the pattern to form a triplet. The interplanar angles between each pair of the bands in the triplets are measured from the Hough transform of the pattern. They are then compared against a list of interplanar angles for the crystal calculated using the information in the crystal database. Thus, the bands are correctly indexed and the crystal orientation determined.

A problem arises when EBSD patterns are obtained using SEMs where the final (objective) electron lens for focusing the electron beam produces magnetic fields near the sample. This problem is particularly significant in "immersion-lens" SEMs where the magnetic fields in the vicinity of the sample are large. Although these magnetic fields are beneficial for image resolution, the fields distort the trajectory of the electrons emerging from the sample. EBSD patterns are distorted by these magnetic fields such that features that would appear ideally as near straight lines, are in practice curved in the EBSD pattern images obtained using an immersion-lens SEM. Therefore, analysis of such distorted EBSD pattern images by the Hough transform is impossible and this particularly limits the usefulness of immersion-lens SEMs for materials analysis.

U.S. Pat. No. 6,555,817 describes a system and method for correcting the distortion in EBSD pattern images which is based upon available empirical information. In a calibration procedure, a sample is used that would give a known pattern with nearly straight lines on an SEM which has negligible magnetic field near the sample. A distorted EBSD pattern is obtained on the immersion lens SEM and displayed on an operator display. A user input device, such as a mouse, is used by the operator to define segments following the curved Kikuchi band in the distorted EBSD pattern and the corresponding segments in the undistorted pattern. The calibration procedure calculates a series of mathematical curves to fit this segmented curved line. The mathematical curves define the amounts by which points along the user-defined curved line must be shifted in order to form a straight line. These correction parameters are saved into a pattern correction parameter data file and used to correct all subsequent patterns obtained from unknown samples.

The calibration procedure requires skill on the part of the user in identifying points along lines in the pattern and is time-consuming. Furthermore, when the field is strong, many bands in the undistorted pattern may not be visible in the distorted pattern because of a large pattern shift. Whereas the Hough transform is a well known procedure for detecting straight lines in images, the automatic detection of weak contrast lines with unknown curvature is a highly specialized and sophisticated pattern recognition problem that does not have a well known solution. The calibration procedure also requires a sufficient quantity of curved lines to be measured over the pattern to ensure that non-uniform distortion can be corrected adequately. Whereas the distortion correction obtained from a single calibration procedure should apply to all subsequent patterns obtained under identical SEM operating conditions, if the SEM accelerating voltage is changed or the specimen height is altered, then a new calibration will be required for the new conditions.

SUMMARY OF THE INVENTION

In accordance with one embodiment of the present invention we provide a method for correcting magnetic field distortions in an electron backscatter diffraction (EBSD) pattern, comprising the steps of:
   obtaining an EBSD pattern generated from a sample placed within an electron microscope;
   calculating the trajectories of electrons in the microscope, for different emergence angles, in accordance with a predetermined representation of a magnetic field in the microscope; and
   calculating a corrected EBSD pattern using the calculated trajectories, the corrected EBSD representing the EBSD pattern if the microscope magnetic field were substantially absent.

One embodiment of the present invention therefore addresses the problems identified above and provides a fast, accurate and versatile method of correcting EBSD patterns in electron microscopes.

The predetermined representation of the magnetic field may describe the magnetic field in the region between the sample and the detector of the microscope and, according to one embodiment of the present invention, relates to the vicinity of the sample.

The EBSD pattern could take a number of forms although, according to one embodiment of the present invention, it is represented by an array of picture elements so that an image can be formed of the pattern. The elements can correspond to individual elements of the detector system such as a digital camera.

In order to correct the EBSD pattern, typically the step of calculating the corrected EBSD comprises calculating the position at which the electrons would have impinged upon a detector of the electron microscope in the substantial absence of the microscope magnetic field. An uncorrected image may then be corrected by calculating how the trajectories of the electrons in the magnetic field resulted in the image embodied in the picture elements.

Various types of electron microscope may be used with the method, including scanning electron microscopes. The method finds particularly advantageous application with "immersion lens" scanning electron microscopes. The microscope magnetic field is therefore typically a leakage field from one or more magnetic lenses.

The representation of the magnetic field may take a number of forms. For example the representation of the microscope magnetic field may be a database of magnetic field strengths and directions at a number of spatial positions in microscope. These may be as a result of modeling or measurement. According to one embodiment of the present invention a model of the microscope magnetic field is used. We have found that good results can be obtained using a representation of the magnetic field in the form of at least one magnetic dipole. Such models may comprise a plurality of dipoles arranged in a ring about the optical axis.

Although such models could be entirely theoretical in nature, according to one embodiment of the present invention, they comprise one or more parameters such that they may be fitted to experimental data, such as measured values of the magnetic field in the microscope. Detailed magnetic modeling software could also be used to provide data to which the model is fitted.

In selecting such parameters the model is typically fitted so as to provide a difference in crystal orientations calculated using test EBSD patterns obtained in the presence of and in substantially the absence of the microscope magnetic field, which is below a predetermined threshold or indeed minimized. Alternatively, these patterns themselves can be compared. The absence of the field is approximated well by the use of a relatively low microscope magnification (where the objective lens current is relatively low). A relatively high magnification causes the presence of the magnetic field. A low magnification EBSD image can be compared with a corrected high magnification image to select the correct model parameters. The position and magnetic field strength of the magnetic dipole may be used as such parameters.

The model parameters may be adjusted in accordance with the working distance, specimen height or microscope accelerating voltage. Test patterns may be used to set the parameters of the model in each case.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

BRIEF DESCRIPTION OF THE DRAWINGS

Some examples of the present invention will now be described with reference to the accompanying drawings.

FIG. 9A shows an example field immersion SEM EBSD at low magnification.

FIG. 9B shows the example field immersion SEM EBSD at high magnification, illustrating distortion.

FIG. 10A is an example of under-correction of the EBSD pattern.

FIG. 10B shows a fully corrected EBSD pattern.

FIG. 10C shows an over-correction of the EBSD pattern.

DETAILED DESCRIPTION

The present invention uses a representation of the magnetic field in the vicinity of the sample to calculate trajectories for electrons backscattered from the sample. The calculations are used to find how an EBSD pattern will be distorted and provides a method for re-mapping the pattern into the form it would take in the absence of the field. Conventional techniques such as the Hough transform can then be applied to analyse the corrected pattern.

Figure 1:
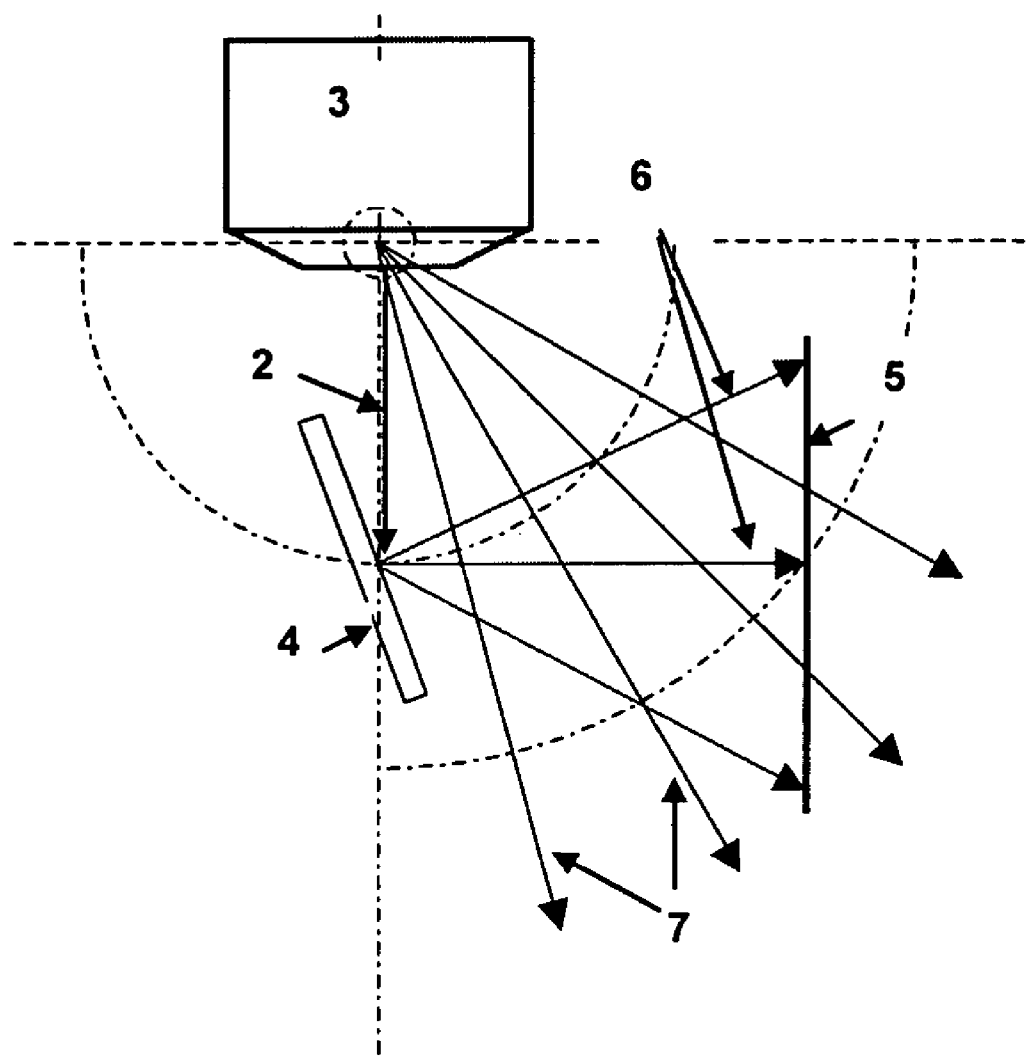
FIG. 1 is a schematic representation of an SEM arrangement for obtaining a backscatter diffraction pattern.

FIG. 1 is a simplified representation of the components of an SEM configured to perform EBSD pattern analysis. Electrons in the form of an incident electron beam 2 pass through a magnetic lens 3 and impinge upon a sample 4 having a surface inclined at an angle to the beam direction. Electrons received from the sample impinge upon a phosphor screen 5. Although a single final objective lens 3 is shown, additional magnetic lenses may be present to reduce aberrations. Although the following text will refer to a single objective lens the invention can be applied to any configuration where there is a significant magnetic field in the vicinity of the sample. This magnetic field is sometimes referred to as the "leakage magnetic field" to contrast the situation with conventional SEMs where the field is constrained to be within the metal housing of the lens. It is also sometimes referred to as the "immersion" field, again to distinguish the situation from a conventional SEM where the sample is in a field free region.

The details in terms of the field geometry and strength of the leakage magnetic field below the objective lens are not usually known, however for a good SEM objective lens the field would have a radial symmetry about its optic axis. Without the stray magnetic field the elastically scattered electrons would travel in straight lines starting from the point on the sample 4 that is struck by the focussed incident beam and moving towards the phosphor screen 5 where the EBSD pattern is formed. This is shown by the arrows at 6. However, in the presence of a magnetic field the trajectories of charged particles bend due to the Lorentz force denoted by the vector cross product (ev×B) where e is the charge on the electron, v is the vector velocity, and B is the vector magnetic field strength. The leakage magnetic field is shown schematically by the arrows at 7.

Figure 2:
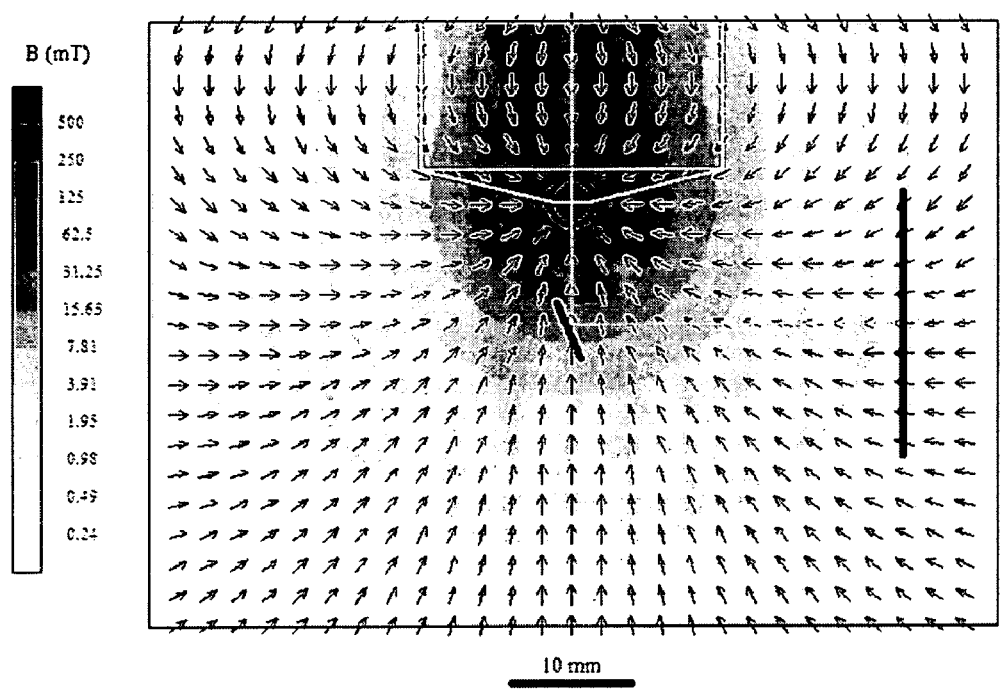
FIG. 2 shows a typical leakage magnetic field.

In the general case, the magnetic field varies in strength and direction. This is shown diagrammatically in FIG. 2 as a 2D section where the small arrows indicate the field direction at different positions and the shaded contours indicate the strength of the field.

Since electrons that form Kikuchi bands have essentially the same energy as the incident beam, the magnitude of velocity can be calculated as the electron starts its trajectory from the sample. The initial direction is chosen so that with a straight trajectory, the electron would strike the phosphor at position $(x_0, y_0)$; thus the initial vector velocity v is determined in magnitude and direction. If the field strength and direction, B, can be predicted at any position, then the initial force on the electron can be calculated and this determines the acceleration. As will be understood by one of ordinary skill in the art, by considering a small increment of time or distance along the trajectory, the change in direction of the electron can be calculated so that the new position and velocity of the electron is now predicted at the end of this increment. By repeating this calculation in a series of increments, the trajectory of the electron can be followed until it reaches the plane of the phosphor at position (x,y).

Figure 3:
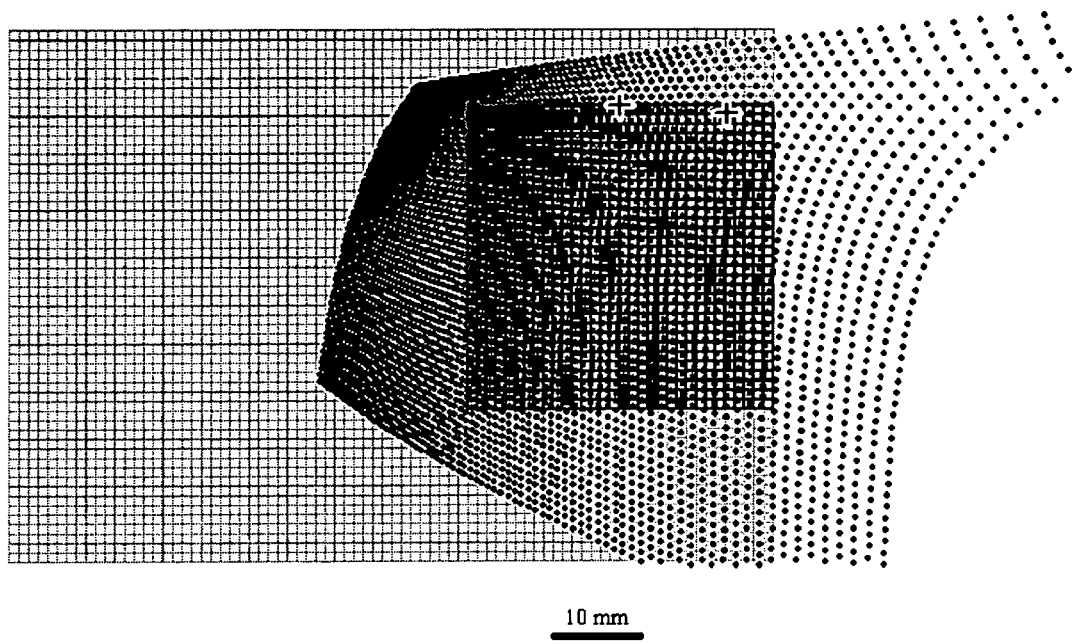
FIG. 3 shows the relationship between electron trajectories in the presence and absence of the leakage magnetic field.

In the FIG. 3, the large rectangular grid starting at the left shows where the backscattered electrons would reach the plane of the phosphor in the absence of any leakage field. The dots moving out to the right show where these same electrons would reach the plane of the phosphor when the field is present, each dot corresponding to a crossing point on the rectangular grid. The square area in the centre shows the physical position of the phosphor which effectively defines a rectangular grid of picture elements imaged by a digital camera. For every trajectory that finishes within a picture element at (x,y) on the phosphor, the corresponding position that the electron would have reached in the absence of the field, $(x_0, y_0)$, is stored. For picture elements where no trajectory ends, the $(x_0, y_0)$ value is interpolated from values in the vicinity.

Figure 4:
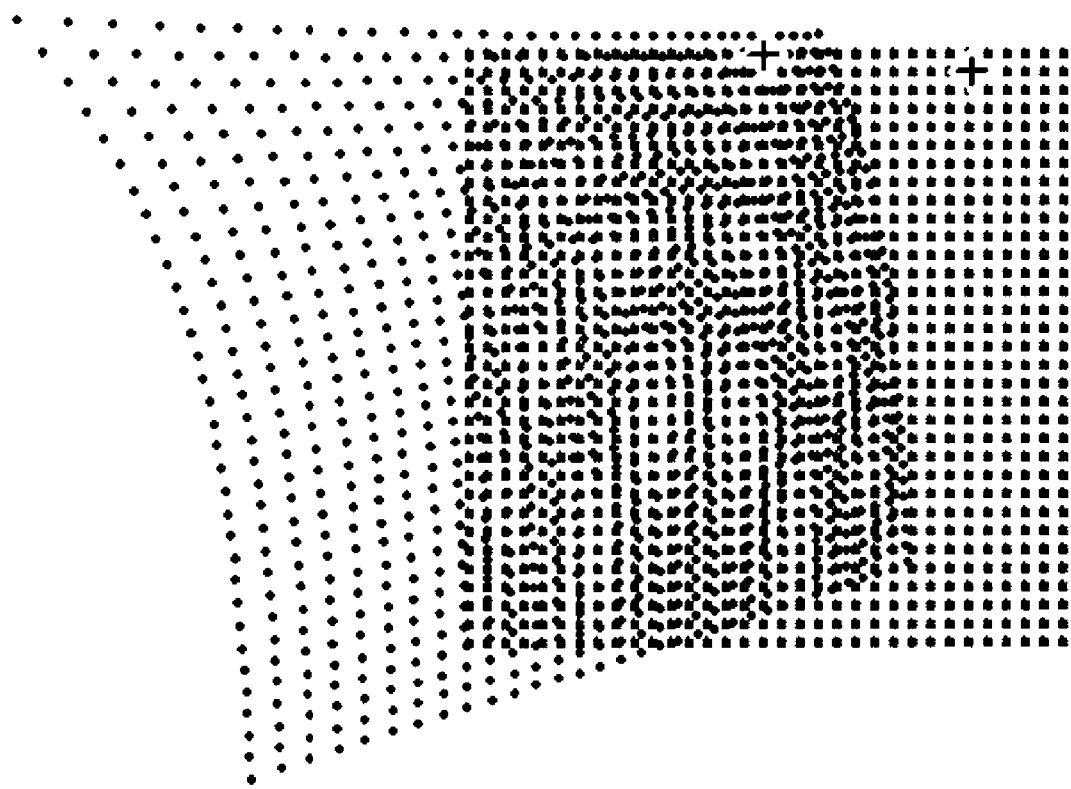
FIG. 4 shows the origins of the electrons in a received grid.

Thus, for every picture element a correction is stored that shows where electrons contributing to this picture element would have struck the plane of the phosphor in the absence of a field. In this example as is shown in FIG. 4, the square image grid of picture elements recorded from the phosphor is now mapped into the non-square grid of picture elements towards the left of the figure. It will be appreciated that the present invention is not limited to the rectangular and square grids as described here.

As FIG. 4 illustrates, the re-mapped picture elements are no longer spaced on a uniform grid. For subsequent analysis of the image it is more convenient to have a uniform array of corrected picture elements and intermediate positions are therefore assigned intensity values by interpolating from nearby picture element intensities.

Figure 5:
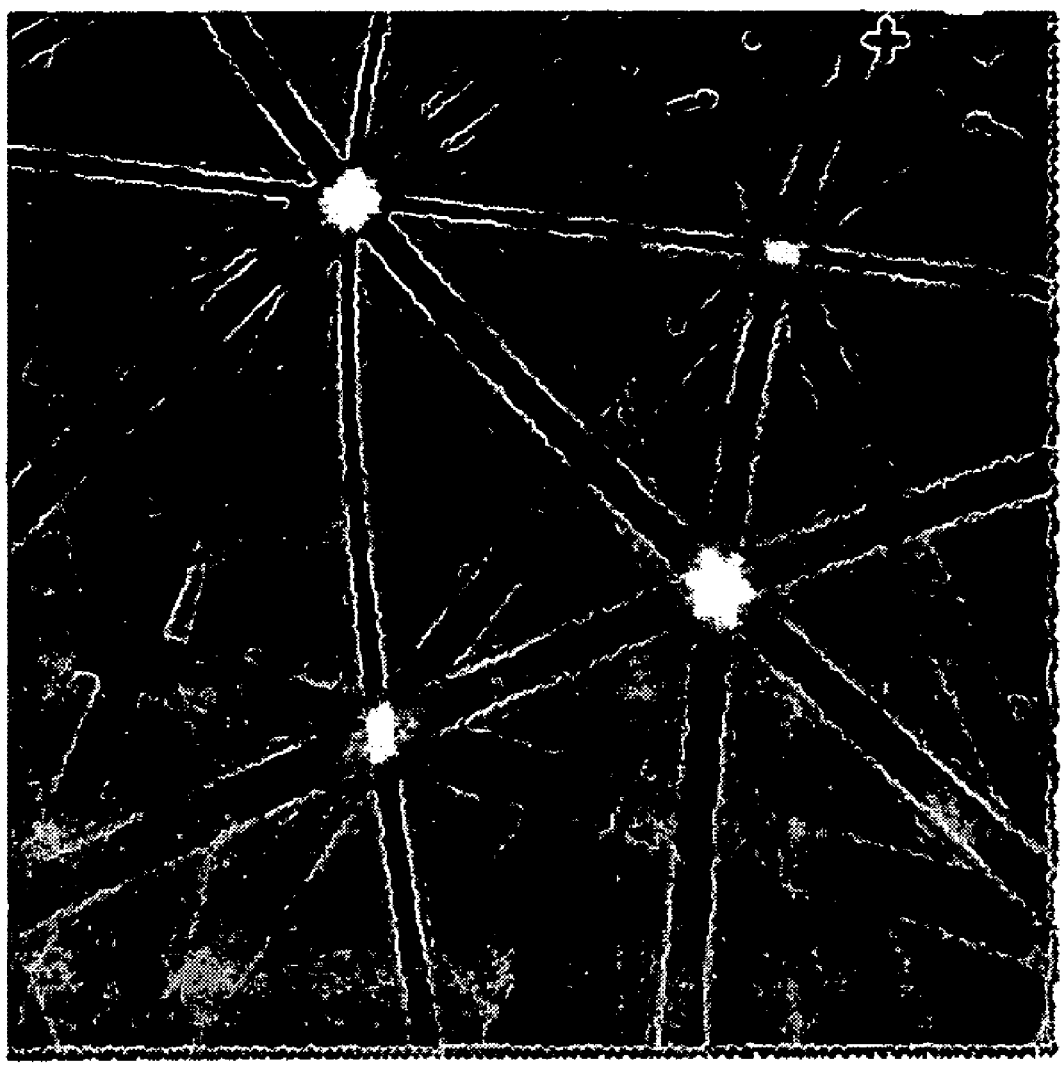
FIG. 5 shows a typical distorted EBSD for Germanium.

When a known crystalline sample such as Ge generates an EBSD pattern on the phosphor, the bending of the Kikuchi bands is apparent. This is shown in FIG. 5.

Figure 6:
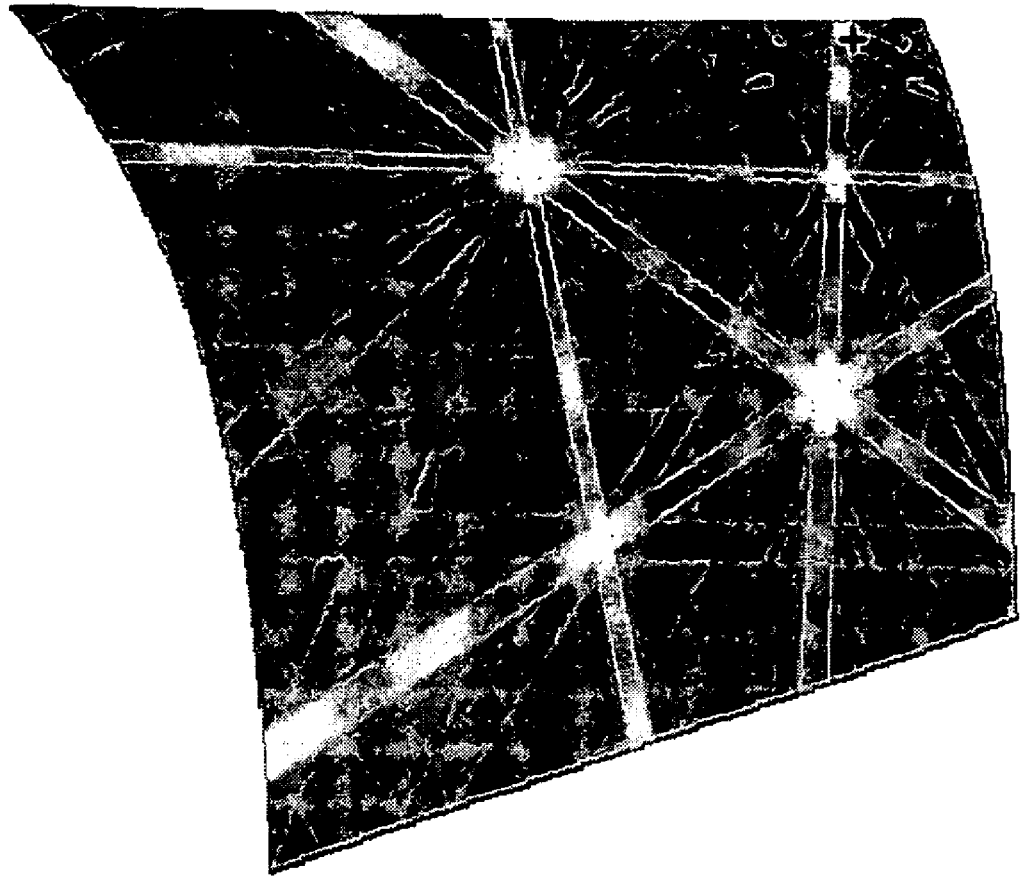
FIG. 6 shows a corresponding corrected EBSD.

When the picture elements are re-mapped as described above, the corrected pattern (FIG. 6) shows that the Kikuchi bands have now been straightened out and the resulting pattern can now be analysed using for example the Hough transform to find the location and angles for intersecting bands.

Key to the method is the determination of the magnetic field distribution. Microscope lenses are usually designed with field modelling software and in one example the manufacturer of the electron microscope could generate a database describing the vector magnetic field for different lens currents. The data could be generated from calculations. Alternatively, it is possible to measure the field strength at a number of positions in the chamber. However, in both cases, it would be useful to obtain values of the field at all the conditions likely to be used in practice and it is not always possible to obtain field strengths at enough positions to provide an accurate trajectory calculation. The approach described here is to model the field using one or more magnetic dipoles. The position, separation and strength of the dipole used is then adjusted to provide the best approximation to the field.

Figure 7:
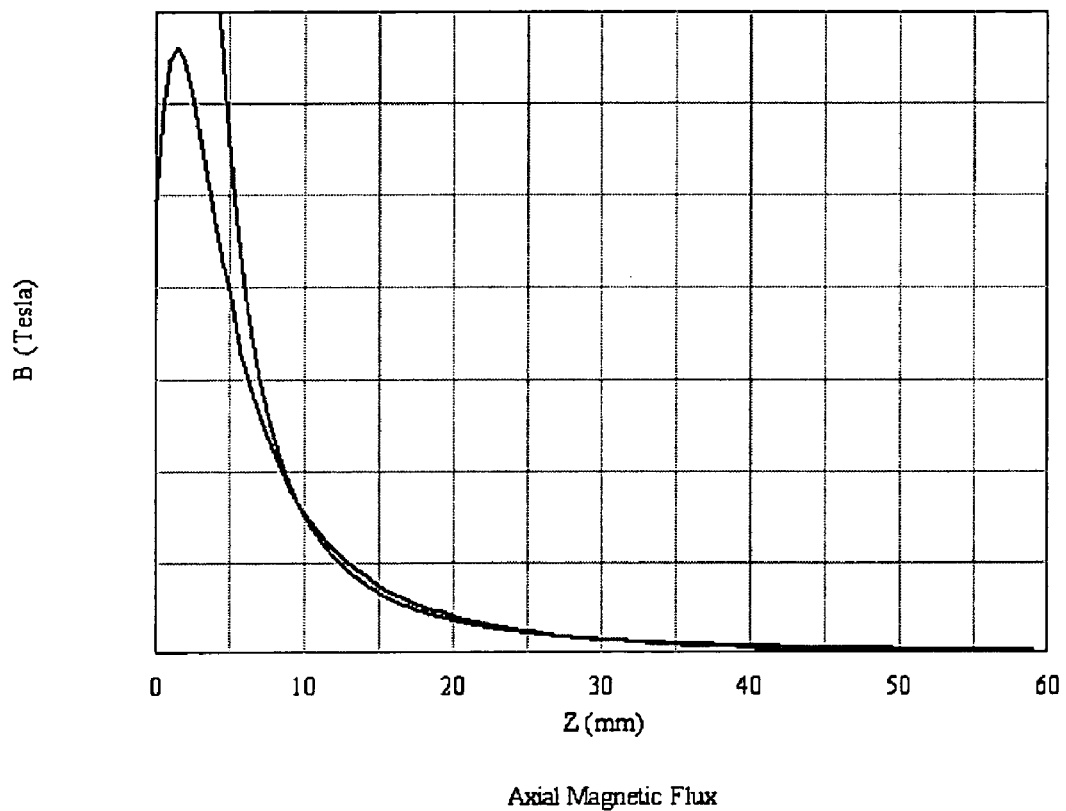
FIG. 7 shows a comparison between the axial magnetic field strength of a magnetic lens and a magnetic dipole.
Figure 8:
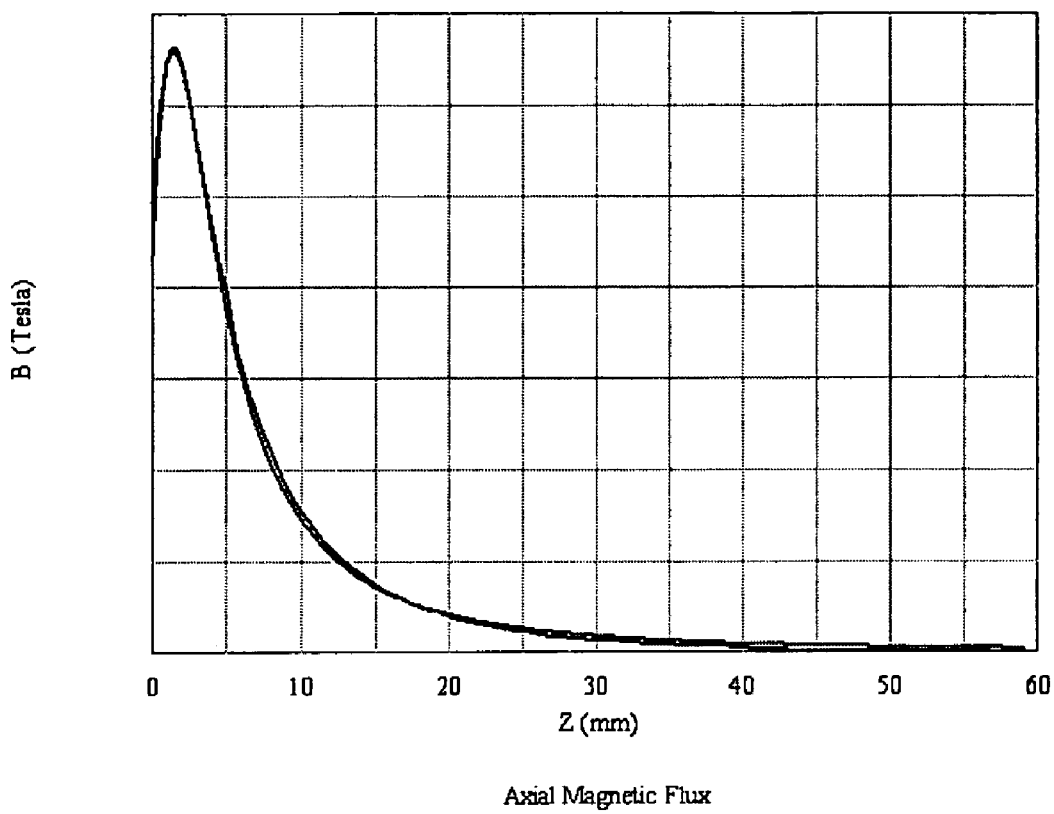
FIG. 8 shows how a magnetic lens can be modelled with a circular distribution of magnetic dipoles.

In FIG. 7, the axial magnetic field strength for an objective lens (curve showing a peak) is compared to the approximate field generated by a magnetic dipole with 20 mm separation of the poles. For distances more than 10 mm from the pole piece, it can be seen that the approximation is quite good and may be sufficient to correct patterns when the working distance is much greater than 10 mm. More elaborate models can provide a much more accurate fit to the real field distribution. In FIG. 8 a circular distribution of 16 dipoles, each with 40 mm in length, and a circle diameter 7 mm provides a fit to the microscope lens field that would be suitable for correcting distortion over a wide range of working distances.

More complex models require more calculation time. A single dipole approximation, where the length, position and strength of the dipole can be varied, may be adequate in some cases. Whatever model is chosen, the parameters, in particular dipole strength, should be optimised. While this optimisation can be chosen to provide the best fit to an experimental or modelled field distribution, a method is described below where the parameters are deduced by a calibration procedure involving measurement of EBSD patterns from a known sample.

When a field immersion SEM works at low magnification (LM) mode, the EBSD pattern is relatively undistorted. The distorted pattern taken at the high magnification (HM) mode under the same voltage and working distance is paired with the LM pattern, as shown in FIGS. 9A and 9B. FIG. 9A is the undistorted LM pattern taken at 20 kV and WD=15 mm. FIG. 9B is the distorted HM pattern taken at the same kV and WD.

In this example we assume that the pattern distortion in FIG. 9B is due to a magnetic field of a dipole with a given lower monopole location, LML, and a dipole field strength, $B_0$ at a distance $r_0$ from the monopole. Then this field can be used to relate the distorted patterns with undistorted patterns using the trajectory calculation method described above. As an illustration, the effects of under, approximately correct and over estimation of the field are shown in FIGS. 10A, 10B and 10C respectively, although in practice, an objective method for choosing the optimal field is beneficial.

A different field strength $B_0$ is used to correct the distorted pattern in FIGS. 10A to C. FIG. 10A is under-corrected, $B_0$=5.6 tesla. FIG. 10B is fully corrected, $B_0$=8.6 tesla. FIG. 10C is over-corrected, $B_0$=11.6 tesla.

One method to optimise the model parameters is to identify the so called "pattern centre" in the LM pattern using a conventional EBSD calibration procedure. The "pattern centre" is the point in the plane of the phosphor where the undistorted electron trajectory would intercept the plane at normal incidence. If this point falls on the phosphor, recognisable features near the "pattern centre" can be used to locate the corresponding position in the HM pattern. The field model parameters are then adjusted to give the required change to the electron trajectory that matches the apparent movement of the pattern centre.

A more sensitive method of adjusting the field parameters involves solving the corrected patterns for different values of the field parameters. When a distorted HM pattern is fully corrected, the crystal orientation obtained from this pattern (using for example a Hough transform and subsequent analysis) should be identical to that determined by using the undistorted LM pattern of the same sample. In practice if the misorientation between the crystal orientations determined from HM and LM patterns is less than 1°, the pattern correction is usually adequate.

Figure 11:
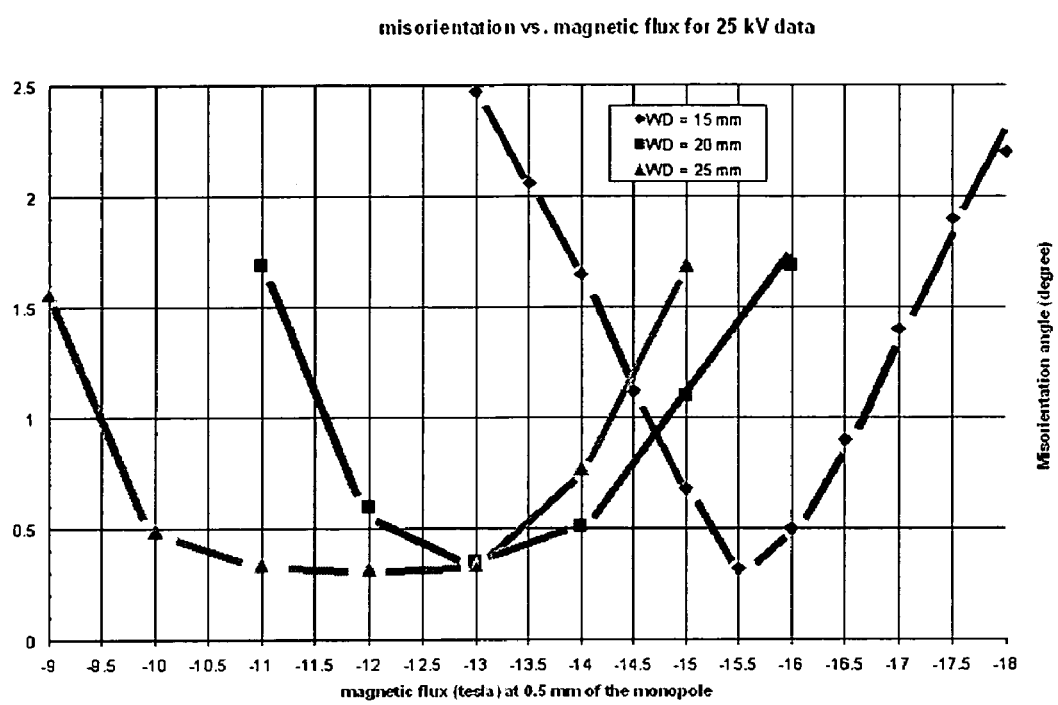
FIG. 11 illustrates the relationship between misorientation and field strength for three working distances.

In the following example, the field strength for correcting a distorted HM pattern is determined by plotting the misorientation vs. field strength. The patterns taken at 25 kV and three different working distances are used to calculate the field strengths for a particular dipole position in the microscope. This is shown in FIG. 11. The minima of the curves indicate that lower monopole field strengths of −15.5, −13, and −12 tesla can be used to correct the HM patterns at these working distances in order to achieve less than 0.5° orientation difference between analyses using LM and corrected HM patterns.

Figure 12:
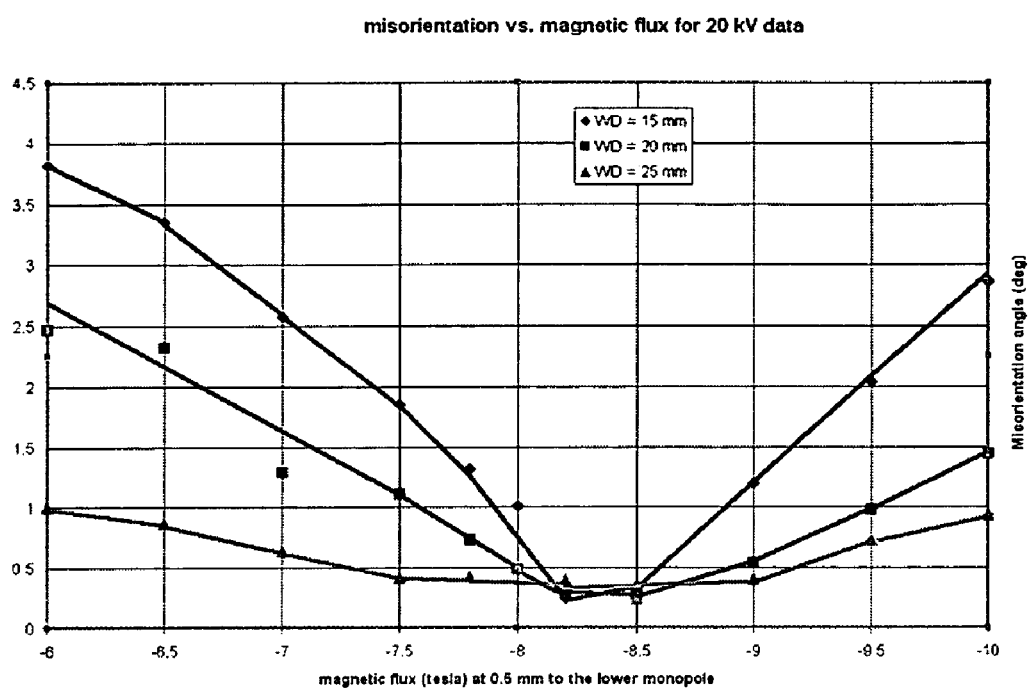
FIG. 12 shows how different magnetic dipole positions can be used with differing specimen heights.

In some microscope configurations it is possible to vary the specimen height while keeping the leakage field constant. In this case, the monopole strength that gives the minimum misorientation between LM and corrected HM patterns may vary with specimen height. Although this may provide an adequate correction, if the leakage field is always the same, the ideal field model would be independent of the height position where the beam strikes the specimen. However, by choosing a suitable dipole position relative to the final lens, the field strength that can correct patterns taken at different specimen heights can be brought to the same value. This is shown in FIG. 12 for 20 kV patterns. The minima of the misorientation for distorted patterns taken at different specimen heights are achieved by the same field strength −8.5 tesla.

Patterns acquired at a series of SEM accelerating voltages may be similarly used to find parameters of the dipole models that give adequate pattern correction.

The procedure used in the more sensitive method of adjusting the field parameters (mentioned above) involves solving the corrected patterns for different values of the field parameters. This procedure can be summarised by the following method steps:

Obtain a "reference" electron backscatter diffraction pattern in LM mode (that is with substantially no distortion);

Tune the EBSD parameters so as to be able to solve the reference pattern obtained in (1) wherein solving the pattern comprises enabling the Kikuchi bands to be detected and indexed;

Obtain a distorted EBSD pattern from the same location as in (1) but in this case, using HM mode;

Select the field parameters for the model, so as to provide a magnetic flux distribution;

Apply the field parameters selected in (4) to the HM pattern in an attempt to correct the pattern;

Using the pattern "corrected" in (5), calculate the misorientation with respect to the orientation of the "reference" LM pattern in (2); and;

Repeat steps (4) to (6) by selecting the field parameters in (4) (such as magnetic flux) so as to obtain a desired level of misorientation between the solution of the "corrected" and "reference" patterns.

It will be appreciated that the field parameters selected may depend upon the model chosen to represent the magnetic field within the microscope. One of these parameters may be varied, such as the magnetic field strength, or in more complex cases, multiple parameters may be varied. The field parameters selected for variation may be modified according to a predetermined sequence. Although it is desirable to fully minimise the misorientation, so as to maximise the accuracy of the correction, in practice a threshold of misorientation may be set below which the correction is deemed sufficiently small and therefore acceptable. This may depend on the end use of the corrected patterns.

In another example, we have realised that the desired field parameters for the model can be obtained without requiring the solution of either a "reference" or "distorted" electron backscatter diffraction pattern. Instead, the raw patterns are correlated so as to obtain the best fit between the two. This method is as follows:—

Obtain a "reference" electron backscatter diffraction pattern using LM mode;

Obtain a "distorted" electron backscatter diffraction pattern from the same position on the specimen as in (i), although this time using HM mode;

Select appropriate field parameters to apply to the distorted pattern;

Apply the selected parameters in order to "correct" the distorted pattern;

Compare the "corrected" pattern directly with the "reference" pattern; and

Repeat steps (iii) to (v) whilst changing the field parameters using the "Golden Ratio" (or equivalent) minimisation algorithm so as to obtain a sufficient correlation between the corrected and reference patterns.

Again, as in the method described earlier, a threshold may be set below which the correlation between the patterns is deemed sufficient. The "Golden Ratio" algorithm can be found in for example: Press, W. H., Teukolsky, S. A., Vetterling, W. T., and Flannery, B. P., 1999, Numerical Recipes in C, The Art of Scientific Computing, second edition, Cambridge University Press, Cambridge, United Kingdom.

In the above method therefore, it is the patterns themselves that are compared rather than the index attributed to such patterns, in order to obtain the appropriate "correction" field parameters. It will be appreciated that corresponding areas of the respective patterns need to be compared.

These examples demonstrate that a simple dipole model for magnetic field can be used to obtain corrected patterns that can be solved using conventional EBSD techniques. Furthermore, suitable parameters for the model can be obtained by a calibration procedure that does not require the user to identify corresponding features in two images and these parameters can be determined by looking for a function minimum, a procedure that is easy to automate.

The description shows how knowledge of the immersion magnetic field can be used effectively to calculate pattern distortion. Access to the detailed lens design and lens modeling tools would be an advantage but the simple dipole approximations can still be optimized to provide adequate pattern corrections when the field is not exactly known.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A method for correcting magnetic field distortions in an electron backscatter diffraction (EBSD) pattern, comprising the steps of:

obtaining an EBSD pattern generated from a sample placed within an electron microscope;

calculating the trajectories of electrons in the microscope, for different emergence angles, in accordance with a predetermined representation of a magnetic field in the microscope; and calculating a corrected EBSD pattern using the calculated trajectories, the corrected EBSD pattern representing the EBSD pattern if the microscope magnetic field were substantially absent.

2. A method according to claim 1, wherein the predetermined representation of the magnetic field relates to the vicinity of the sample.

3. A method according to claim 1, wherein the EBSD pattern is represented by an array of picture elements.

4. A method according to claim 1, wherein the step of calculating the corrected EBSD comprises calculating the position at which the electrons would have impinged upon a detector of the electron microscope in the substantial absence of the microscope magnetic field.

5. A method according to claim 1, wherein the electron microscope is an immersion lens scanning electron microscope.

6. A method according to claim 1, wherein the microscope magnetic field is a leakage field.

7. A method according to claim 1, wherein the representation of the microscope magnetic field is a database of magnetic field strengths and directions at a number of spatial positions in the microscope.

8. A method according to claim 1 wherein the representation is a model of the microscope magnetic field.

9. A method according to claim 8, wherein the model is a model of at least one magnetic dipole.

10. A method according to claim 9, wherein the model comprises a plurality of dipoles arranged in a ring.

11. A method according to claim 8, wherein the model is fitted to measured values of the magnetic field in the microscope.

12. A method according to claim 8, wherein the model is fitted to values of the microscope magnetic field calculated by magnetic field modeling software.

13. A method according to claim 8, wherein the model is fitted such that the difference between test EBSD patterns obtained in substantially the absence of the microscope magnetic field and as corrected using the model, is below a predetermined threshold.

14. A method according to claim 13, wherein the model is fitted to provide the said difference in crystal orientations by performing the steps of:

i) Obtaining a reference electron backscatter diffraction pattern using low magnification mode;

ii) Obtain a distorted electron backscatter diffraction pattern from the same part of the sample, using high magnification mode;

iii) Select appropriate field parameters to apply to the distorted pattern;

iv) Apply the selected parameters so as to produce a corrected pattern;

v) Compare the corrected pattern with the reference pattern; and vi) Repeat steps (iii) to (v) whilst changing the field parameters using a minimization algorithm so as to obtain the desired correlation between the corrected and reference patterns.

15. A method according to claim 13, wherein the said difference is minimized.

16. A method according to claim 13, wherein the test patterns are obtained at a series of specimen heights.

17. A method according to claim 13, wherein the test patterns are obtained at a series of microscope accelerating voltages.

18. A method according to claim 8, wherein the model is fitted such that the difference in crystal orientations calculated using test EBSD patterns obtained in the presence of and in substantially the absence of the microscope magnetic field, is below a predetermined threshold.

19. A method according to claim 18, wherein said presence and absence of the magnetic field are produced using relatively high and low microscope magnifications respectively.

20. A method according to claim 18, wherein the difference in crystal orientations is determined between a test EBSD obtained in substantially the absence of the magnetic field and a corrected EBSD based upon a test EBSD in the presence of the magnetic field and the model.

21. A method according to claim 20, wherein the model is fitted to provide the said difference by:

1) Obtaining a reference electron backscatter diffraction pattern in low magnification mode;

2) Tuning the EBSD parameters so as to solve the reference pattern obtained in (1);

3) Obtaining a distorted EBSD pattern from the same location using high magnification mode;

4) Selecting one or more field parameters to define the model;

5) Applying the selected field parameters to the HM pattern so as to produce a corrected pattern;

6) Using the pattern corrected in (5), calculating the misorientation with respect to the orientation of the reference pattern in (2); and 7) Repeating steps (4) to (6) by selecting different field parameters so as to obtain the desired level of misorientation between the solution of the corrected and reference patterns.

22. A computer program disposed on a computer readable medium for correcting magnetic field distortions in an electron backscatter diffraction pattern, said program comprising: a means for obtaining an actual electron backscatter diffraction pattern generated from a sample placed within an electron microscope; a means for calculating trajectories of electrons in said electron microscope, for different emergence angles, in accordance with a predetermined representation of a magnetic field in said electron microscope; and a means for calculating a corrected electron backscatter diffraction pattern using said trajectories of electrons and said actual electron backscatter diffraction pattern, the corrected electron backscatter diffraction pattern representing a theoretical electron backscatter diffraction pattern from said sample in said microscope with said magnetic field substantially absent.

* * * * *